United States Patent
Seguin et al.

(10) Patent No.: US 6,211,393 B1
(45) Date of Patent: Apr. 3, 2001

(54) COMPOUNDS WITH BIOLOGICALLY ACTIVE SILICON AND APPLICATIONS

(75) Inventors: Marie Christine Seguin; Jean Gueyne, both of Monaco (MC); Jean-Francois Nicolay, Villefranche-sur-mer; Andre Franco, Menton, both of (FR)

(73) Assignee: Exsymol S.A.M., Monaco (MC)

( * ) Notice: Subject to any disclaimer, the term of this patent is extended or adjusted under 35 U.S.C. 154(b) by 0 days.

(21) Appl. No.: 08/652,429

(22) PCT Filed: Sep. 29, 1995

(86) PCT No.: PCT/FR95/01266

§ 371 Date: Jul. 22, 1996

§ 102(e) Date: Jul. 22, 1996

(87) PCT Pub. No.: WO96/10575

PCT Pub. Date: Apr. 11, 1996

(30) Foreign Application Priority Data

Sep. 30, 1994 (FR) .................................. 94 12088

(51) Int. Cl.$^7$ .................. C07F 7/08; C07F 7/10
(52) U.S. Cl. .................. 556/410; 556/413; 556/418; 556/419; 556/426; 556/411; 514/64; 514/844; 514/944; 424/401; 424/457; 424/78.03
(58) Field of Search ...................... 502/413, 418, 502/419, 426, 410, 411; 514/648, 844, 944; 424/401, 457, 78.03

(56) References Cited

U.S. PATENT DOCUMENTS 3,546,267   12/1970   Ishmail .
5,648,511 * 7/1997   Ng et al. .................. 556/410 X

FOREIGN PATENT DOCUMENTS

| | | |
|---|---|---|
| 2929225 | 2/1980 | (DE) . |
| 3240971 | 5/1984 | (DE) . |
| 0136501 | 4/1985 | (EP) . |
| 0148398 | 7/1985 | (EP) . |
| 0227025 | 7/1987 | (EP) . |
| 0273266 | 7/1988 | (EP) . |
| 0295983 | 12/1988 | (EP) . |
| 0368481 | 5/1990 | (EP) . |
| 0395433 | 10/1990 | (EP) . |
| 2314724 | 1/1977 | (FR) . |
| 2335232 | 7/1977 | (FR) . |

* cited by examiner

Primary Examiner—Paul F. Shaver
(74) Attorney, Agent, or Firm—James C. Lydon

(57) ABSTRACT

Silicon compound of general formula a), in which A, B, C, D are radicals which are different from OH and are covalently bonded to Si; two or three of these bond that are linked to Si are Si—O—C, Si—S—C or Si—N—C type bonds and are hydrolyzable in vivo, forming Si—OH bonds that are biologically active especially when in contact with living tissue, the A and D bonds of formula b) being invariably hydrolyzable; at least one of the hydrolyzable bonds corresponds to an acyloxy, aryloxy or vinyloxy radical; at least one of the compounds obtained after hydrolysis of the hydrolyzable bonds is a stabilizer, and the non-hydrolyzable bonds, which are of the Si—C type, correspond to hydrocarbon or fluorocarbon radicals for which Si is not directly linked to the phenyl ring.

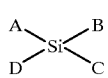

(a)

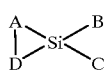

(b)

23 Claims, No Drawings

COMPOUNDS WITH BIOLOGICALLY ACTIVE SILICON AND APPLICATIONS

SUMMARY

Compound with silicon with the general formula:

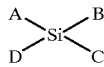
a)

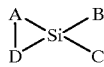
b)

in which
- A, B, C, D are radicals different from OH linked to Si by covalent bonds,
- two or three of these bonds with Si are bonds of Si—O—C Si—S—C or Si—N—C type, hydrolysable in vivo with formation of Si—OH bonds biologically active, especially when in contact with living tissues, the links A and D of the formula b) always being hydrolysable.
- at least one of the hydrolysable bonds corresponds to an acyloxy, aryloxy or vinyloxy radical
- at least one of the compounds obtained after hydrolysis of the said hydrolysable bonds is a stabilizer, and
- the non hydrolysable links are of Si—C type and correspond to hydrocarbon or fluorocarbon radicals for which Si is not directly bound to a phenyl ring.

TECHNICAL FIELD

The present invention concerns compounds with biologically active silicon, especially when in contact with alive tissues, as well as the therapeutic and cosmetic applications of these compounds.

STATE OF TECHNIQUE

Silicon is a very common element in nature and is generally known under its natural inorganic forms such as silica and silicate, and also under the form of synthetic polymers, the silicones. These silicon compounds are barely soluble or not at all soluble in aqueous medium which explains their weak incidence at the alive organisms level. The silicones, in particular, are characterized by a great inertia towards the biological medium and consequently present a high biocompatibility.

However, the silicon, even in minute quantities, plays an important biological role and must be considered as an essential element of life. It is especially necessary for a normal growth of numerous species. It has been demonstrated that silicon was intervening in the connective tissues structuration in interacting with the glycosaminoglycan and proteins. This is one of the constitutive elements of proteins-glycosaminoglycan complexes found in the extracellular matrix of these tissues. Silicon also interacts with the glycosaminoglycan in the cartilage tissue development. We also know that silicon plays an important role in the bone formation where it favours the mineralization process.

Besides, silicon can be considered as a collagen constituent and we think that it plays a major role in the reticulation process of collagen fibres.

Silicon is also involved in the cell metabolism and it would be especially favourable to the metabolic activity of osteoblasts.

Beyond the cross-linking power of silicon and its implication in the metabolic activity of some cells, it appears that a high silicon content, in the tissues, jointly with the glycosaminoglycan content is characteristic of healthy and metabolically active tissues.

Today's researches tend to reinforce the idea that silicon intervenes in numerous biological mechanisms. Recent works have even demonstrated that silicon plays a major role, in the aluminium elimination by biological systems.

Works of the applicant have demonstrated that silicon compounds could constitute a form of assimilable silicon by the organism (as opposed to mineral silicon or to silicones) on condition that it possesses the characteristic of existing in aqueous solution under the form of soluble oligomers of low molecular weight. Furthermore, another necessary characteristic of the oligomers activity in aqueous solution is to present numerous Si—OH functions. So, it is obvious that the biological properties of these assimilable compounds by the organism, are only observed if they form soluble oligomers in aqueous solution, which result from a chain of siloxane bonds Si—O—Si, rich in Si—OH functions.

Apart from the fact that the presence of Si—OH highly polar functions, confers their water solubility to the oligomers, at the present time, we think that a part of the properties observed are conducted by the fact that the chemical species involved in most of the above mentioned biological mechanisms would be a form of silicon, the silicic acid, of Si $(OH)_4$ formula. This compound only exists in very low concentrations in water since it has a very strong tendency to polycondense to form silica.

Consequently we have researched more stable products similar to silicic acid, by chemically modifying the Si—OH functions. It quickly became obvious that these functions were essential for the biological activity. In other respects, we knew that a series of natural compounds, and among them, the tannins and the catecholamines were able of forming a complex with the silicic acid and like this were able of increasing its stability in solution. These complexes would be the way of transport for the silicic acid in the organism and it is under this form that the cell would introduce the silicon. Nevertheless, their stability is still too weak for the carrying out of a pharmacologically active product.

SUMMARY OF THE INVENTION

That is why the main object of the invention is to provide compounds with silicon possessing biologically hydrolysable links especially when in contact with living tissues and that will allow one to obtain oligomers possessing the biologically active Si—OH functions.

A compound that meets this requirement has the general formula:

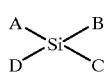
a)

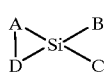
b)

in which
- A, B, C, D are radicals different from OH linked to Si by covalent bonds,
- two or three of these bonds with Si are bonds of the Si—O—C—, Si—S—C or Si—N—C type, hydrolysable in vivo with the formation of biologically active Si—OH bonds especially when in contact with living tissues, the links A and D of the formula b) always being hydrolysable,

- at least one of the hydrolysable bonds corresponds to an acyloxy, aryloxy or vinyloxy radical
- at least one of the compound, obtained after hydrolysis of the said hydrolysable functions is a stabilizer
- the non hydrolysable functions are of the Si—C type and correspond to hydrocarbon or fluorocarbon radicals for which Si, is not directly linked to a phenyl ring.

DESCRIPTION OF THE INVENTION

In the compound of the invention as above defined, the radicals which are hydrolysable biologically are consequently radicals linked to Si by an oxygen atom, a nitrogen atom or a sulphur atom. When a silicon atom is directly bound to an oxygen atom, these radicals are preferably acyloxy radicals or aryloxy radicals (such as phenoxy radicals) or even vinyloxy radicals. This preference can be explained by the fact that it is necessary to obtain the release of at least one stabilizer after the hydrolysable bonds hydrolysis. The best stabilizers are the carboxylic acids resulting from the acyloxy radicals hydrolysis, the phenol resulting from the aryloxy radicals hydrolysis and the enol resulting from the vinyloxy radicals hydrolysis.

When the silicon is linked by a sulphur atom, the hydrolysable radicals are preferably thioester or aryl or alkylthioether radicals.

When the silicon is linked by a nitrogen atom, the hydrolysable radicals are preferably amines, mono or disubstituted by hydrocarbon chains substituted or not by one or several functional groups, or by aryl or alkylamides.

The radicals linked to Si and which are not hydrolysable are those presenting a Si—C bond and they can be hydrocarbon radicals such as alkyl radicals, alkenyl, arylalkyl and aryl however excluding phenyl type of aryl radicals. This exclusion is justified by the fact that the phenyl-Si—OH type compounds obtained after hydrolysis of hydrolysable links, present negative effects on live organisms and are especially toxic in regard to liver, pancreas, bone marrow and the heart muscle (see the article "Bioactive silane and siloxanes" by R. R. Le Vier in the Chemical Bulletin, March 1986, pages 89–91). The non hydrolysable radicals can also be fluoroalkyl or fluoroalkenyl types of fluorocarbon radicals.

We shall notice that all the other types of biologically non hydrolysable bonds are excluded and especially the Si—O—Si bonds known for their chemical inertia and their absence of reactivity in regard to biological mediums.

Examples of compounds according to the invention are given here below:

Salicylic Alcohol Derivatives (or 2-hydroxybenzylalchohol):

2-oxo-benzyloxy-ethoxymethylsilane

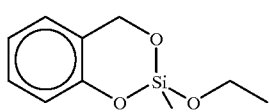

2-oxo-benzyloxy-dimethylsilane

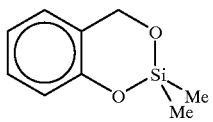

Alpha-hydroxyacids Derivatives:

Ethoxymethylsily-2-oxo-octanoate

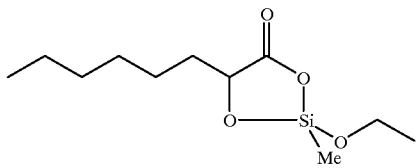

Dimethylsilyl-2-oxo-octanoate

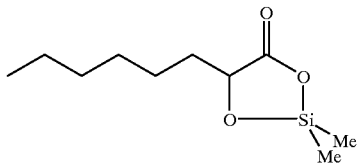

2,2-ethoxymethyl-4-oxo-5-methyl-1,3-dioxa-2-cyclosilane or ethoxymethylsilyl-lactate:

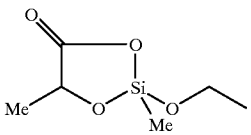

Amino Acids Derivatives:

2,2-dimethyl-4-oxo-5-amino-1,3-dioxa-2-cyclosilane (or dimethylsilyl-L-serine)

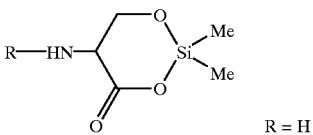

R = H

Dimethylsilyl-L-hydroxyproline:

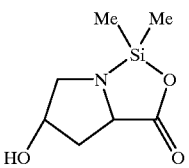

Dimethylsilyl-L-methionine:

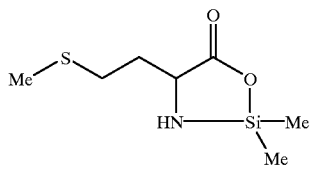

Derivatives of Long-chain Acids:
Dimethyldidecanoyloxysilane:

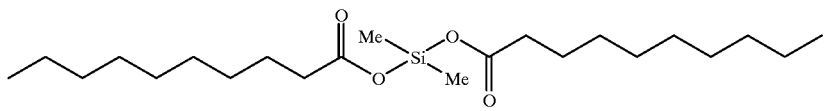

Methylsilanetridecanoylester:

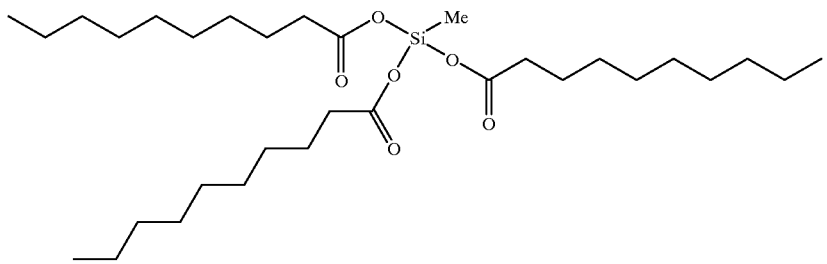

Caproyldiethoxysilane:

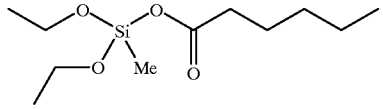

Salicylic Acid Derivatives:

2,2-methyl,tertbutoxy-4-oxo-1,3-dioxa-2-silane:

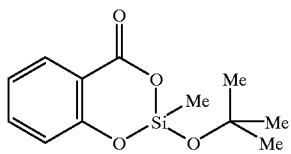

2,2-dimethyl-4-oxobenzo-1,3-dioxa-2-silane:

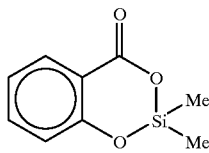

2,2-ethoxy, n-octyl-4-oxobenzo-1,3-dioxa-2-silane

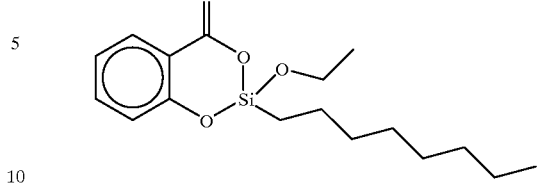

2,2-dimethyl-4-oxo-(3-octanoylbenzo)-1,3-dioxa-2-silane:

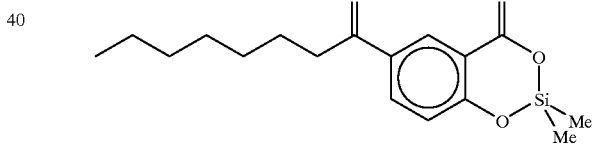

Miscellaneous:
Dimethylsilyl-2,3–5,6-ascorbate:

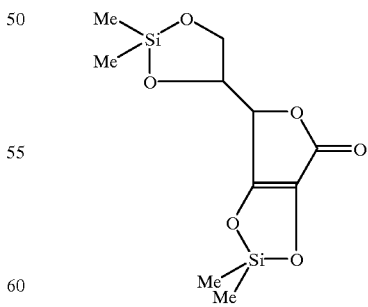

Later on, we shall call silyl the biologically active compound containing two or three Si—OH bonds, and we shall admit that these compounds which are the subject of the invention, are silyl "precursors" merely called precursors in the rest of the description.

The methods of compounds preparation according to the invention are multiple. They use as starting material commercially available "functionalized" silanes such as chlorosilanes, e.g. tetrachlorosilane $SiCl_4$, alkoxysilanes as tetraalkoxysilane $SiOR_4$, hetero-functional silanes as trichlorosilane $Cl_3SiH$ or functionalized alkylsilanes in order to reduce the number of synthesis steps like the dimethyldichlorosilane, the methyltrietoxysilane, etc.

Consequently the precursors according to the invention are biologically inactive compounds, able, after topical, oral or systemic administration to change into a biological active compound, spontaneously or with a specific enzymatic catalyst such as silicase.

If we consider a single hydrolysable bond of the precursor (knowing that two or three links are hydrolyzed the same way), the following transformation occurs when in contact with living tissues such as skin, mucosa, or a biological fluid.

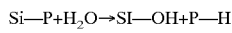

$$Si\text{—}P + H_2O \rightarrow Si\text{—}OH + P\text{—}H$$

As it has been previously mentioned, the —Si—OH compounds being in an aqueous medium, have a tendency to form soluble oligomers through the condensation of two, three or few molecules condensation —Si—OH compounds. It is obvious that if this compound only contains a single OH bond, such condensation ending in dimers, the Si—OH bonds would disappear. Therefore it is necessary for the precursors, according to the invention, to have at least two hydrolysable bonds.

The P—H product obtained in the preceding reaction can be an inactive non toxic compound or a compound being able to favour, reinforce or complete the silyl action.

One collective characteristic of the precursors, essential in the carrying out of the invention, is that the P—H product obtained after hydrolysis plays a role as a stabilizing agent. It protects the silyl activity in counteracting their polycondensation leading to the formation of water insoluble and then inactive compounds.

After hydrolysis, the stabilizing agent is released in the medium and stabilizes the silyl creating with it weak bonds (hydrogen bonds). The stabilizing power of some of these agents can also be explained by their ability to form again a transitory covalent bond. We then obtain a dynamic structure where some bonds possess a "mixed character" (hydrogen bond, covalent bond).

The stabilizers complying with the above stated criterion, are after hydrolysis, simple carboxylic acids (which ester are the precursors), preferably possessing a carbon chain superior to 5 carbon atoms, this thanks to their ability to form micellar structures able to stabilize the silyl, phenol (which phenoxy radicals are the precursors), especially prone to form transitory covalent bonds, and particularly polyfunctional compounds such as hydroxy carboxylic acids compounds and especially alpha and beta hydroxyacids, the glucuronides, the hyroxylated or phenolic amino acids such as serine, threonine or tyrosine, compounds possessing several alcohol (or phenol) functions and above all vicinal alcohol (or phenol) functions. We can quote in this category glycol, the catechol and catecholamine (DOPA, adrenalin) the polyethyleneglycol, the polyol as glycerol, the monosaccharides (L-threose, L-ribose, sorbitol . . . ); phenolic acids such as gallic acid, 3,4-dihydroxybenzoic acid or caffeic acid, and esterified derivatives; diacides such as malonic acid; some compounds possessing a particular geometry adapted to stabilize the silyl complexes in aqueous medium, as the tropolone (ex: thujaplicine).

Consequently, an important characteristic of the invention is the fact that at least one of the radicals linked to a silicon atom is able to release by hydrolysis a stabilizing compound as above defined.

In vivo, the hydrolysis reaction can spontaneously occur without a catalyst. The rate of silyl formation is going thee to depend on several factors:

the pH: an acidic or basic environment increases highly the reaction rate the presence of an enzymatic catalyst is going to specifically increase the hydrolysis speed of some hydrolysable bonds the chemical structure of the precursor the amount of water present in the medium, the temperature the presence of salts or biological molecules possessing an active hydrogen.

One of the characteristic of the precursors, is that they are soluble in non polar mediums:organic solvent, oils, silicones . . . in opposition to the "silyl" highly polar form, soluble in the aqueous phase and insoluble in oils. As far as most or the precursors are quickly hydrolyzed when in contact with water to form silyl, those products offer a large versatility for the formulation, especially for the incorporation in an emulsion.

Consequently, we shall use the precursors in anhydrous formulations. The silyl will only be formed in situ, when in contact with the target organ. This presents some advantages since the lipophilic products cross better some biological barriers.

The polarity modification can also be done in a way that the active silyl preserves an affinity for the nonpolar mediums after hydrolysis. This is the case with the 2,2-ethoxy, n-octyl-4-oxobenzo-1,3-dioxa-2-silane.

The forms of the lipophilic precursors are, without water, stable on a large range of temperature and at all concentrations. They can be used pure whereas the corresponding silyl forms need a stabilizer or a complexing agent, are only stable at a high dilution in a more narrow range of temperature.

One of the important characteristics of these products is that it is possible to modulate the sensitivity of the precursor to the hydrolysis, by modulating its chemical structure. Indeed, if some precursors are hydrolyzed by the single contact with the atmospheric humidity, it is perfectly possible, at the opposite, to obtain stable precursors in aqueous mediums at pH conditions close to neutrality. These latter can be useful when a selective release of the active constituent is researched, for example at the time of an hydrolysis at the gastric level.

If the precursor hydrolysis is not too fast, it is possible to obtain a prolongation of the effect. This "delayed effect" applies in particular to the sequentially deprotected precursors (the hydrolysable bonds are of different chemical natures).

Incidentally, the precursor formation can result in the stabilization of some compounds used as a P protective groups for the silyl, which can be useful when P—H possesses a biological activity.

Therefore, the precursors will be able to be used in the lipid phase of an emulsion, under the form of oily gels, creams or ointments for the topical administrations, both for the therapeutic or cosmetic applications, or under the form of capsules for the oral administration in the therapeutic treatments, or also under the form of intramuscular injections.

Generally speaking, the compounds according to the invention, will be able to be used in numerous applications requiring the properties of the "silyl" forms, that is to say the therapeutic, dietetic or cosmetic properties resulting from the anti-inflammatory, regenerating, anti-degeneration, normalizer, metabolic stimulator, anti-free radical and anti-glycation activity, and again generally speaking for the stimulating activity of the organism's defences.

The following examples are illustrative (but not restrictive) of the formulations used as medicine or cosmetic products in order to demonstrate the above stated activities.

EXAMPLE 1
Regenerating—Anti-inflammatory Activity Arthrosis Treatment

This example concerns the treatment for the chronic arthrosis and the secondary arthrosis, by oral administration of dimethylsilyl-L-hydroxyproline, ($C_7H_{13}NO_3Si$ of M.M.= 187.27). The interest is to bring very important quantities of SiOH and hydroxyproline, which activity is potentialized by SiOH.

The tested compound contains 15% of Si, that correspond to 24% of SiOH.

The shock treatment consists of a per os administration of three capsules per day containing 0.23 g of active principle in three intakes for 3 weeks, then two capsules per day for 1 month. The treatment continues with the administration as a course treatment of one capsule a day.

A study has been carried out on the effects of the dimethylsilyl-L-hydroxyproline on the chondroformation (thymidine $^3(H)$ incorporation, collagen II and PG production) and on the chondroresorption (basal PGE and interleukin 6 production). This study has been done on human chondrocytes in culture during a period of time of 4, 8 and 12 days. PG and interleukin are dosed by radioimmunoassay. The cell multiplication is evaluated by a radiometric method.

A dose-dependent positive effect of the silyl on the synthetic activity of the osteoblasts has been observed through the increase of the alkaline phosphatase activity. In addition, we have noted that the ratios of thymidine incorporation increase of 51% after treatment.

However, the most outstanding effect lies in the very notable reduction of interleukin 6, an inflammation tracer, in the chondroresorption phases. This effect (dose-dependent) is very significant of the silyl anti-inflammatory and regenerating activity. An important reduction of the prostaglandin quantities has been correlatively observed.

EXAMPLE 2
Regenerating Activity Restructuration of the Microvessels

In this example, we have formulated capsules for oral administration with dimethyldidecanoyloxysilane (M.M.= 400.67) corresponding to an SiOH equivalent of 11.5%, in order to improve the venous and lymphatic microcirculation by acting on the capillary coats.

We have manufactured some capsules n°5 with a dissolution of 40% of active in peanut oil, which corresponds to an intake of 0.03 g of silyl per capsule. These capsules have been used in dietetic by persons complaining of having heavy legs. The administration has been of one to two capsules a day. The tests have been carried out on 15 persons of more than 70 years old.

Twelve persons have told about the disappearing of the pains and of the reduction of the vesperal oedema of the ankles. On these twelve persons, three have regained (they say) the legs of their twenties.

On the opposite, the three others persons integrated in this assay, did not have any results, which corresponds to 20% failure.

EXAMPLE 3
Anti-inflammatory, Anti-oedematous, Analgesic and Restoring Activities Dermo-pharmaceutical Composition The experimentation has been carried out on serious erythemas using 2-oxo-benzyloxy-dimethylsilane of M.M.= 180.28, which is equivalent to 25% of SiOH.

2-oxo-benzyloxy-dimethylsilane has been diluted at 25% in isosteraryl benzoate which previously has been incorporated on the basis of 10% in an oily gel, and this, in order to re-establish the protective hydrolipidic film and to stimulate, by the silicon, the skin regeneration. This silicon supply being very important it has allowed to positively intervene on erythema more or less "oedematous" and on the pain resulting of cutaneous tissues damages.

| The gel tested has the formula: | |
|---|---|
| 2-oxo-benzyloxy-dimethylsilane at 25% | 10.00 |
| Sodium lanolate | 12.00 |
| Aluminium stearate | 1.00 |
| Vaseline oil | 100.00 |

The assay has been carried out on 10 persons affected by a serious erythema solare with the freedom of applying the gel as often as wanted.

We have obtained in 80% of the cases, a stop of the pain, a reducing of the oedema in less than 6 hours, and a reducing of the redness of more than 50% in 24 hours, which is very positive.

On the other hand, this oily gel has been used after cobalt therapy sessions on mucous membranes.

We have observed a superficial protection of these mucous membranes with a reducing of the pain and inflammation.

EXAMPLE 4
Anti-inflammatory Action Sport's Man Tendinitis Treatment

It has been performed an oily cream for massages. The massages have been done by massage kinesitherapists, the assays have been carried out on Tennis-Elbows.

The tested compound was the 2-oxo-benzyl-oxydimethylsilane of M.M.=180.28, which is equivalent to 25% SiOH.

We have just incorporated 8% of a pure product in a lano-vaseline which is an extremely fatty cream, allowing a long massage until almost penetration.

The results of the experimentation on twelve persons affected by the Tennis-Elbows are the following:

The patient must rest from 14 to 21 days, during which 3 times a day, he must massage the painful part of the body with the cream.

Four Out of the 12 patients have seen a disappearing of their pain at the end of 6 days and have been able to go back to their daily lives, 5 at the end of 12 days, 1 at the end of 14 days and 2 at the end of 16 days.

With this cream, it has been possible to intervene on tendinopathy, either under shoulder scapular, or supraspinal, or on biceps.

These tendinopathies were revealing a simple painful shoulder or an hyperallergic shoulder with sharp pain.

The experimentation has been done on 12 patients which have been treated 3 times a day.

2 patients having a tendinopathy have been relieved at the end of 5 days, 3 at the end of 9 days, 1 patient affected by an hyperallergic sharp painful shoulder has been relieved at the end of 7 days, 1 at the end of 12 days, 3 at the end of 15 days and 2 have not seen any change of their state.

EXAMPLE 5

Normalizing Action Asthenia Treatment

In this example, we have used the Ascorbosilyl or dimethylsilyl-2,3,5,6 ascorbate, having the formula $C_{10}H_{16}O_6Si_2$, that is to say 24.56% Si, which is equivalent to 32% SiOH.

This compound has been studied for the reshaping, the struggle against the ageing process and tired spells.

The formulation has been carried out in dietetic by per os administration of capsules containing 0.5 g of active.

The interest is to bring very important amounts of silyl; that is, up to 0.19 g of SiOH and 0.31 g per capsule of ascorbic acid.

We have carried out a diluted form of 20% of ascorbosilyl in soja oil, which gives 0.04 g of silyl and 0.07 g of ascorbic acid for each intake. The administration is of 1 to 3 capsules a day.

This compound allows to bring per os quantities which would be impossible in the case of a classical silyl obtained by complexation.

The intake of these capsules has given very quick results in some cases with a recovering of physical health since the eighth day. In other cases, the response came only 3 or 4 months later, but with a change of the behaviour in all the cases, a return to the feeling of well-being and a better adequation to the daily life.

EXAMPLE 6

Metabolic Stimulation Activity Slimming Composition

The compound used has been the dimethyl-silyl-methionine with the formula $C_7H_{15}NO_2SSi$ with M.M.=205.34 releasing 22% of SiOH after in vivo hydrolysis.

We have elaborated an oily gel containing 1% of methionine silyl (0.2% in SiOH) The formulation has been:

| | |
|---|---|
| Silylmethionine | 1.00 g |
| Poly oxoaluminum stearate | 5.00 g |
| Steraric acid | 1.50 g |
| Oleic acid | 0.50 g |
| Vaseline oil q.s.p. | 1.00 g |

This gel has been applied on localized adiposity areas in the evening at the time of going to bed by soft massages until complete absorption.

5 women from 35 to 55 years old have participated in this test.

3 results have been good, reduction from one to two sizes at the end of 3 months.

1 average result of improvement of the skin has been obtained without significant slimming, and on the other way one result has been void.

EXAMPLE 7

Anti-free Radical Activity Usage in Colour Cosmetics

The tested compound has been ethoxymethyl silyl-2-oxo octanoate of M.M.=246.7, which is equivalent to 19% of SiOH.

This compound has been diluted in evening primrose oil on the basis of 45%.

This solution has been used on the basis of 7% in mascaras and lipsticks, which correspond to supply 1% of SiOH.

The goal of these cosmetics was to ensure regeneration, protection of the mucous membrane and sensitive epidermis.

This has been proved by the following test which measures the inhibition percentage of the level of oxidation of the control.

The test consists in producing oxygenated free radicals by an enzymatic way (xanthine oxydase action on the acetaldehyde) and in comparing the cells resistance (cultured with or without ethoxymethylsilyl-2-oxo-octanoate) when in contact with these free radicals. The free radicals addition within the cell culture induces a cytotoxicity. This toxicity results in a cell lysis with an increase of the cell lactate deshydrogenase (LDH). The evaluation of the cell resistance to the cell stress is obtained by the LDH activity dosage by UV spectrophotometry. We measure, where OD indicates the optical density, the LDH activity by the means of the following ratio:

$$\frac{OD \text{ reference} - OD \text{ assay}}{OD \text{ assay}} = 100$$

Results:

We observe a very notable protective effect of silyl. The peroxidative system used has produced superoxide ions and hydrogen peroxide. The study of the results show that silyl induces a protection against the spontaneous cell lysis (LDH activity reduced of 73%). This protection persists and intensifies itself (LDH reduction of 77%) with an induced radicalar stress.

EXAMPLE 8

Anti-glycation and Anti-free Radical Activity Cataract Treatment

The dimethylsilyl-2,3,5,6, ascorbate (or ascorbosilyl) of formula $C_{10}H_{16}O_6Si_2$ with M.M.=288.4 representing 24.56% of Si, which is equivalent to 32% of SiH has been used in ophthalmology as an anti-cataract medicine.

The ascorbosilyl is incorporated on the basis of 6.5% in an ophthalmic ointment composed of a mixture of vaseline and vaseline oil.

The ascorbosilyl after hydrolysis when in contact with the tear flow and the cornea progressively act as an anti-free radical, preventing the cell membrane lipids peroxidation.

It also contributes to re-structure the proteoglycans and the mucopolysaccharide constituents of the cornea.

It should be noted that the presence of the ascorbic acid potentializes the anti-free radical action seeing that it is a natural constituent of the eye.

The anti-radical activity adapted to an anti-cataract medicine has been verified by the following test:

The test consists in producing oxygenated free radicals by an enzymatic way (xanthine oxydase action on the acetaldehyde) and in comparing the cells resistance (cultured with or without dimethylsilyl-2,3,5,6 ascorbate) when in contact with these free radicals.

The free radicals adding within the cell culture induces a cytotoxicity. This toxicity results in a cell lysis with an increase of the cell lactate deshydrogenase (LDE). The evaluation of the cell resistance to the free radical stress is obtained by the LDH activity dosage by UV spectrophotometry.

Results:

We observe a very notable protective effect of the dimethylsilyl-2,3,5,6 ascorbate. The silyl activity is evaluated from the variations of LDH activity in regard to a control experiment. The peroxidative system produces superoxide ions and hydrogen peroxide. The study of the results show that dimethylsilyl-2,3,5,6 ascorbate induces a protection against the spontaneous cell lysis (LDH activity reduced of 67%). This protection persists and intensifies itself (LDH reduction of 79%) in the presence of a radicalar, stress.

EXAMPLE 9
Anti-glyeation Activity Treatment of the Arteriosclerosis Artheriopathies The compound chosen has been the 2,2-dimethyl-4-oxo-5-amino-1,3-dioxy-cyclosilane or dimethylsilyl-L-serine of M.M.=161.23 which is equivalent to 22% of SiOH.

From this derivative, it has been manufactured capsules n°4 containing a solution with 40% of dimethylsilyl-L-serine in soja oil, so that each capsule brings a SiOH quantity of 0.05 g.

According to the daily administered dose, this adding can go from 1 to 6 and we can put in order to solve small problems that come in the dietetic treatments and life style, until medical treatments.

We have demonstrated the anti-glycation activity of the compound which allows to preserve the arterial tissues.

The non enzymatic glycosylation of the proteins is one of the factors responsible for the sclerosis of the connective tissues.

The chemical reactions concerned in this proteins degradation have been identified. The glycation (non enzymatic glycosylation) between sugars and proteins is done at random of the free aminated proteic sites and form betacetomethylamines bonds (Amadori product). These latter start a series of chemical reactions (Maillard 1912) which result in the progressive increase of the proteins reticulation.

Those irreversible links progressively induce the lost of the properties (elasticity) of the supporting tissues, which explains their sclerosis.

We have perfected an original experimental procedure that allowed us to study in vitro the dimethylsilyl-L-serine specific reactivity in the proteic glycation reactivity phenomenon.

The degree of glycosylation can be evaluated by a colorimetric method specific for the dosage of the glucose—protein formation. This technique allows to demonstrate the 5-hydroxymethyl furfural (HMF) released from the carbohydrate after an acid hydrolysis. The HMF ratio is quantitatively determined by the colorimetric reaction with the acid 2-thiobarbituric (TBA).

Results:

The protein reticulation (albumin) ratio is reduced in a significant way (−37%) when the dimethylsilyl-L-serine is added to the protein solution at the beginning of the reaction. This experimentation confirms the very notable antiglycation biological role of the dimethylsilyl-L-serine.

The product has been tested in dietetic, on 6 persons, all men, under treatment and affected of artheriopathy of the lower limbs. The treatment was being performed for more than 12 months and the intake of one capsule a day therefore has been an additive.

On 4 out of 6 persons, we have noted a notable improvement of the walk perimeter.

What is claimed is:

1. Silicon compound of the general formula:

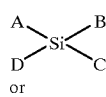

(a)

or

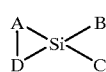

(b)

in which
 A, B, C, D are radicals different from OH linked to the Si by covalent bonds,
 two or three of the covalent bonds with the Si are Si—O—C, Si—S—C or Si—N—C bonds and are hydrolysable in vivo to biologically active Si—OH bonds, provided that the bonds to A and D in the formula b) both hydrolysable,
 the moiety to which at least one of the hydrolysable bonds is connected is an acyloxy, aryloxy or vinyloxy radical,
 the compound after hydrolysis of the said hydrolysable bonds having stabilizer properties, and
 the non-hydrolysable bonds being of the Si—C type and connected to hydrocarbon or fluorocarbon radicals in which the Si is not directly linked to a phenyl ring.

2. Compound according to claim 1, in which at least one said moiety is an acyloxy radical having a carbon chain containing more than 5 carbon atoms.

3. Compound according to claim 1, in which one of said moiety is a phenoxy radical.

4. Compound according to claim 1 which, after hydrolysis, is a hydroxy carboxylic acid, glucuronide, hydroxylated aminoacid or phenolic compound and has stabilizer properties.

5. A composition containing a compound according to claim 1 in a therapeutic, dietetic or cosmetic amount and a carrier therefor.

6. Therapeutic composition according to claim 5, in which the compound is dimethylsilyl-L-hydroxyproline.

7. Therapeutic composition according to claim 6 in a capsule.

8. Therapeutic composition according to claim 5 in which the compound is dimethyldidecanoyloxysilane.

9. Therapeutic composition according to claim 8 in a capsule.

10. Therapeutic composition according to claim 5 in which the compound is oxo-benzyloxy-dimethylsilane.

11. Therapeutic composition according to claim 10 in which the carrier is an oily gel.

12. Therapeutic composition according to claim 5, in which the compound is 2-oxo-benzyloxy-dimethylisilane.

13. Therapeutic composition according to claim 12 in which the carrier is an oily massage cream.

14. Therapeutic composition according to claim 5, in which the compound is dimethylsilyl-2,3,5,6 ascorbate.

15. Therapeutic composition according to claim 4, in which the carrier is an ophthalmic ointment.

16. Therapeutic composition according to claim 5 in which the compound is 2,2-dimethyl-4-oxo-5-amino-1,3-dioxycyclosilane or dimethylsilyl-L-serine.

17. Therapeutic composition according to claim 16, in a capsule.

18. Dietetic composition according to claim 5, in which the compound is dimethylsilyl-2,3,5,6 ascorbate.

19. Dietetic composition according to claim 18 in a capsule.

20. Cosmetic composition according to claim 5, in which the compound is dimethyl silyl methionine.

21. Cosmetic composition according to claim 20, in which the carrier is an oily gel.

22. Cosmetic composition according to claim 5 in which the compound is ethoxymethyl silyl-2-oxo octanoate.

23. Compound according to claim 4 which, after hydrolysis, is selected from the group consisting of alpha hydroxy acid, beta hydroxy acid, serine, threonine, tyrosine, glycol, catechol, catecholamine, polyethylene-glycol, glycerol, L-threose, L-ribose, sorbitol, gallic acid, 3,4-dihydroxybenzoic acid, caffeic acid, malonic acid and tropolone.

* * * * *